US012758356B2

(12) United States Patent
Noell et al.

(10) Patent No.: US 12,758,356 B2
(45) Date of Patent: *Oct. 13, 2026

(54) APPLICATION AID FOR THE TREATMENT OF WOUNDS

(71) Applicant: LOHMANN & RAUSCHER GMBH, Schoenau an der Triesting (AT)

(72) Inventors: Corinna Noell, Hamburg (DE); Wolfgang Harreither, Traiskirchen (AT); Marko Tuertscher, Muntlix (AT)

(73) Assignee: LOHMANN & RAUSCHER GMBH, Schoenau An der Triesting (AT)

( * ) Notice: Subject to any disclaimer, the term of this patent is extended or adjusted under 35 U.S.C. 154(b) by 1235 days.

This patent is subject to a terminal disclaimer.

(21) Appl. No.: 17/154,111

(22) Filed: Jan. 21, 2021

(65) Prior Publication Data

US 2021/0137637 A1 May 13, 2021

Related U.S. Application Data

(63) Continuation-in-part of application No. 16/166,586, filed on Oct. 22, 2018, now abandoned, which is a (Continued)

(30) Foreign Application Priority Data

Apr. 28, 2016 (DE) ..................... 20 2016 002 788.4

(51) Int. Cl.

*A61B 90/80* (2016.01)
*A61B 90/00* (2016.01)
(Continued)

(52) U.S. Cl.

CPC .............. *A61B 90/80* (2016.02); *A61B 90/39* (2016.02); *A61F 13/38* (2013.01); *A61F 15/008* (2013.01);
(Continued)

(58) Field of Classification Search

CPC . A61B 90/80; A61B 90/39; A61B 2090/3966; A61M 3/0279; A61M 35/003; A61M 2205/586
(Continued)

(56) References Cited

U.S. PATENT DOCUMENTS 2,737,702 A 3/1956 Arnold et al.
3,561,441 A 2/1971 Lombardi
(Continued)

FOREIGN PATENT DOCUMENTS

CN 2276333 3/1998
CN 1259024 7/2000
(Continued)

OTHER PUBLICATIONS

Submission in EPO Opposition against EP 2 365 794 B1. Dated Dec. 20, 2013. [No Reference Available—of record in U.S. Appl. No. 13/146,729].

(Continued)

*Primary Examiner* — Andrew J Mensh
(74) *Attorney, Agent, or Firm* — STINSON, LLP

(57) ABSTRACT

The invention relates to a flexible application aid for the treatment of wounds. The application aid can be used in particular for the debridement and/or cleansing of wounds, including the skin surrounding the wound. The application aid according to the invention including a flexible or elastically deformable application wand, facilitates debridement of superficial to deep wounds without the risk of injury to the wound.

32 Claims, 7 Drawing Sheets

Related U.S. Application Data continuation of application No. 15/244,020, filed on Aug. 23, 2016, now Pat. No. 10,149,735.

(51) Int. Cl.

| | |
|---|---|
| ***A61F 13/38*** | (2006.01) |
| ***A61F 15/00*** | (2006.01) |
| ***A61M 3/02*** | (2006.01) |
| ***A61M 35/00*** | (2006.01) |
| *A61B 17/32* | (2006.01) |
| *A61F 13/00* | (2006.01) |

(52) U.S. Cl.

CPC ........ *A61M 3/0279* (2013.01); *A61M 35/003* (2013.01); *A61B 17/32* (2013.01); *A61B 2017/320004* (2013.01); *A61B 2017/320012* (2013.01); *A61B 2017/320072* (2013.01); *A61B 2090/3966* (2016.02); *A61F 2013/00531* (2013.01); *A61M 2205/586* (2013.01)

(58) Field of Classification Search

USPC .......................................................... 604/310

See application file for complete search history.

(56) References Cited

U.S. PATENT DOCUMENTS

| | | | | | |
|---|---|---|---|---|---|
| 3,708,837 | A | | 1/1973 | Chiba | |
| 3,732,125 | A | | 5/1973 | Stroh | |
| 3,732,135 | A | | 5/1973 | Ernst et al. | |
| 4,887,994 | A | * | 12/1989 | Bedford | A61M 35/006 206/229 |
| 4,938,901 | A | * | 7/1990 | Groitzsch | D04H 3/16 604/362 |
| 4,980,943 | A | | 1/1991 | Barber | |
| 5,040,260 | A | | 8/1991 | Michaels | |
| 5,921,251 | A | | 7/1999 | Joshi | |
| 5,953,783 | A | | 9/1999 | Hahn | |
| 6,026,534 | A | | 2/2000 | Gonda | |
| 6,720,058 | B1 | | 4/2004 | Weeks et al. | |
| 6,957,958 | B2 | * | 10/2005 | Rowe | A61C 5/62 206/229 |
| 7,303,804 | B2 | | 12/2007 | Yoshida | |
| 7,540,680 | B2 | | 6/2009 | Feldman et al. | |
| 8,152,929 | B1 | | 4/2012 | Perring | |
| 8,308,702 | B2 | | 11/2012 | Batchvarova et al. | |
| 9,080,267 | B2 | | 7/2015 | Batchvarova et al. | |
| 9,609,983 | B2 | | 4/2017 | McCarthy | |
| 10,149,735 | B2 | * | 12/2018 | Noell | A61M 3/0279 |
| 2002/0090591 | A1 | * | 7/2002 | Fischer | A61C 5/40 433/81 |
| 2002/0122832 | A1 | | 9/2002 | Hanke | |
| 2003/0176827 | A1 | | 9/2003 | Chandra et al. | |
| 2004/0228990 | A1 | | 11/2004 | Hines | |
| 2004/0265534 | A1 | | 12/2004 | Curro et al. | |
| 2006/0039742 | A1 | * | 2/2006 | Cable, Jr. | A61M 35/003 401/133 |
| 2006/0075589 | A1 | | 4/2006 | Choi | |
| 2008/0125687 | A1 | | 5/2008 | Flick et al. | |
| 2008/0177253 | A1 | | 7/2008 | Boehringer et al. | |
| 2009/0226506 | A1 | | 9/2009 | Masters et al. | |
| 2009/0291944 | A1 | * | 11/2009 | Ash | A01N 37/10 514/227.5 |
| 2010/0146724 | A1 | * | 6/2010 | Jo | A46B 9/10 15/167.1 |
| 2010/0228267 | A1 | * | 9/2010 | Mercado | A61B 5/1076 606/131 |
| 2011/0046607 | A1 | | 2/2011 | Halevy | |
| 2011/0193400 | A1 | | 8/2011 | Kwon et al. | |
| 2012/0046670 | A1 | * | 2/2012 | Engl | A61F 13/00 112/475.01 |
| 2014/0188110 | A1 | * | 7/2014 | Weber | A61B 18/149 606/49 |
| 2015/0305945 | A1 | | 10/2015 | Engl et al. | |
| 2015/0366413 | A1 | | 12/2015 | Dudzic et al. | |
| 2016/0066763 | A1 | | 3/2016 | Xu | |
| 2016/0183757 | A1 | | 6/2016 | Xu | |
| 2016/0199566 | A1 | * | 7/2016 | Schug | A61B 17/3203 604/289 |
| 2016/0262590 | A1 | | 9/2016 | Link et al. | |
| 2016/0270970 | A2 | | 9/2016 | Engl et al. | |
| 2019/0142642 | A1 | * | 5/2019 | Burnet | A61L 15/38 600/362 |
| 2021/0007764 | A1 | * | 1/2021 | Wilhelms | A61B 17/54 |

FOREIGN PATENT DOCUMENTS

| | | | | | |
|---|---|---|---|---|---|
| DE | 19839505 | | | 3/2000 | |
| EP | 0552933 | | | 7/1993 | |
| EP | 0632990 | | | 1/1995 | |
| EP | 0874073 | | | 10/1998 | |
| JP | 02239829 | | | 9/1990 | |
| JP | 2009061186 | A | * | 3/2009 | A61F 13/36 |
| RU | 2153838 | | | 8/2000 | |
| RU | 2181024 | | | 4/2002 | |
| WO | WO 98/46818 | | | 10/1998 | |
| WO | WO 98/57570 | | | 12/1998 | |
| WO | WO 2007015729 | | | 2/2007 | |
| WO | WO 2007105883 | | | 9/2007 | |
| WO | WO 2016/038287 | | | 3/2016 | |
| WO | WO 2016/038289 | | | 3/2016 | |

OTHER PUBLICATIONS

"Hansaplast Wundreinigungstuch", www.hansaplast.de (accessed Jan. 2007) . [No Reference Available—of record in U.S. Appl. No. 13/146,729].

Easyderm® , "Easyderm" Total Body Cleansing System, Apr. 2006 . . . [No Reference Available—of record in U.S. Appl. No. 13/146,729].

Enjor , "Enjo for your Home", Catalogue Version 2.1 (Admitted Prior Art—Undated) . [No Reference Available—of record in U.S. Appl. No. 13/146,729].

Interlocutory Decision in Opposition Proceedings dated Mar. 29, 2016, issued in related European Patent Application 10704304.4 (Both the original German and a translated copy) (18 pgs for each document).

* cited by examiner

APPLICATION AID FOR THE TREATMENT OF WOUNDS

CROSS-REFERENCE TO RELATED APPLICATIONS

This application claims priority to and is a Continuation-in-Part of U.S. patent application Ser. No. 16/166,586, filed on Oct. 22, 2018, which is a Continuation of U.S. patent application Ser. No. 15/244,020, filed on Aug. 23, 2016 (now issued U.S. Pat. No. 10,149,735), which is based on and claims priority to German Utility Model No. DE 20 2016 002 788, which registered on Jun. 16, 2016 and is incorporated herein by reference in its entirety.

STATEMENT REGARDING FEDERALLY SPONSORED RESEARCH OR DEVELOPMENT

Not applicable.

BACKGROUND OF THE INVENTION

Field of the Invention

The invention concerns debridement of wounds. Debridement is generally defined as the removal of contaminants, such as dead tissue, debris and exudate as well as scales and keratoses from wounds and the skin surrounding the wound. An objective is to cleanse the wound, to facilitate improved wound monitoring as well as the promotion of healing.

Description of Related Art

The debridement of wounds, in particular of deep wounds, including surgically invasive wounds, such as diabetic ulcers, arterial and venous ulcers, decubital ulcers, postoperative wounds and wounds in secondary healing, traumas, burns and scalds, is typically required for accelerating the healing process and for preventing a secondary infection of the wound.

Conventional application aids however can cause injuries to the wound or the wound environment in use. For example, problems exist with prior art devices due to inappropriate deflection.

In view of these problems, it is the object of the invention herein to provide an application aid designed for the treatment, including debridement and cleansing, of acute and chronic superficial to deep wounds and surgically invasive wounds while providing good cleansing capacity with reduced risk of injuries.

BRIEF SUMMARY OF THE INVENTION

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

Figure 1:
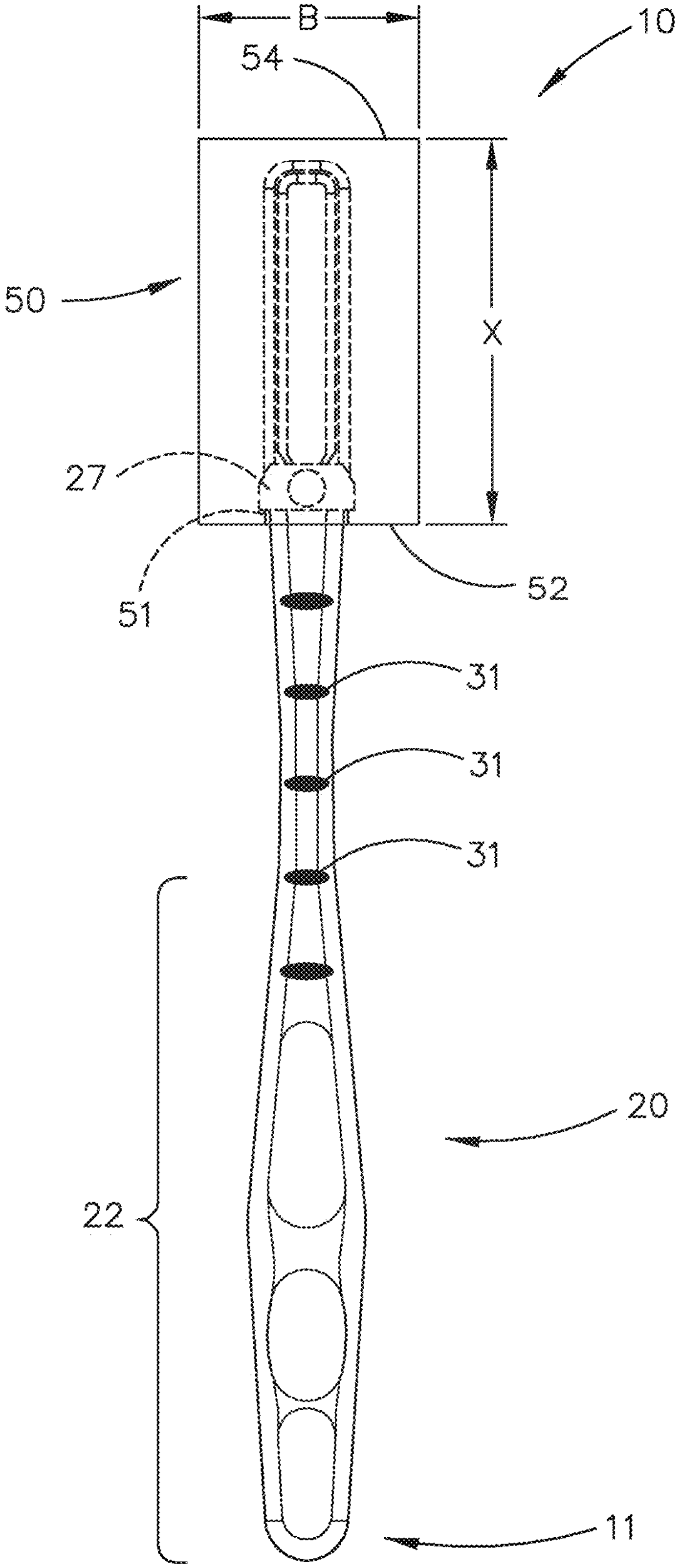
FIG. 1 A schematic upper side view of the application aid according to FIG. 2 also having a wound treatment head according to the invention herein.

The invention relates to an application aid for the treatment of wounds. The application aid shall be used in particular for the debridement and/or cleansing of wounds.

The invention is based on the realization that, especially when used in deep wounds, a rigid application wand can cause injuries if the user treats the wound applying excessive compressive force. A rigid or unyielding application wand may, for instance, cause pressure points or tears in the wound environment when inserted into a deep wound or moved therein. In contrast, the flexible application wand of the application aid according to the invention yields if the user applies excessive force so that an injury of the wound and the wound environment can be prevented.

Preferably, upon exerting a bending force in a transverse direction of the wand, the application wand of the application aid according to the invention becomes flexibly or elastically deformed, until it reaches an elasticity limit. In other words, the application wand reversibly bends when subjected to a bending force perpendicular to the longitudinal direction of the application wand and returns to its original state when the application of force is removed. It has been discovered that by using the application aid according to the invention with the flexible, notably an elastically deformable application wand, debridement of superficial to deep wounds is possible without the risk of injury to the wound. Longitudinal direction as used herein means the dimension from the front end 12, to the rear end 11 of the application wand 20, as exemplified in FIG. 3 at "L".

Handling of the application aid according to the invention can be enhanced by designing a rear section 71 of the application wand as a grasping handle section 22 which may, for instance, have the shape of a grasping handle. In some embodiments, the grasping handle section is curved and/or fluted in order to enhance the grip. The grasping handle section has, for instance, undulations for inserting fingers and extending in the longitudinal direction of the application wand. Slipping of the application wand relative to the user's hand can be reliably prevented.

A front section 72 of the application wand can be designed as a fastening section 24 for fastening a wound cleansing head 50, and in this arrangement, the wound cleansing head can, for instance, be a wound cleansing wipe or a wound cleansing pad. After fastening the wound cleansing head to the fastening section, the wound cleansing head can preferably completely encircle or envelope the fastening section. This assures that only the wound cleansing head, but not the front end 12 of the application wand, comes into contact with the wound tissue. The term wound cleansing wipe or wound cleansing pad denotes herein a flat textile structure, including cotton, non-woven and woven fabrics, etc., which, depending on the need and depending on the application, consists of natural and/or synthetic fibers and has the desired cleansing properties.

The flexibility of the application wand can be enhanced by having, arranged between the grasping handle section and the fastening section, a bending section 26 with increased flexibility. Preferably, for increased flexibility, in the bending section, the application wand may have a wand cross section, which is reduced compared to the grasping handle cross section (Exemplary is FIG. 6*b*), and/or at least one notch or depression extending in a direction transverse to the longitudinal direction of the application wand (Exemplary is FIG. 6*c*).

In the interest of good cleansing capacity when used in deep wounds, it has proven to be expedient to have the grasping handle section extend over more than ⅓ and less than ⅔ of the length of the application wand and/or to have the fastening section extend over more than ⅕ and less than ⅓ of the length of the application wand. For a total application wand length between 14 cm and 18 cm, the grasping handle section may, for instance, extend over a length between 6 cm and 10 cm and/or the fastening section over a length between 4 cm and 6 cm, in particular approximately 5 cm. The fastening section will preferably be completely covered or enveloped by the wound cleansing head 50.

Not only excessive rigidity of the application wand but also excessive flexibility may prove to be disadvantageous in wound treatment. Excessive flexibility of the application wand may, for instance, cause the user to lose the feeling for the force of the application. The user may, for instance, believe to be already expending the force required for obtaining a desired cleansing capacity, while, in fact, as a result of a high deflection of the application wand, the pressure necessary for the application is not achieved.

A particularly good cleansing capacity can be achieved using an application wand, which undergoes a flexural elongation of 5% when subjected to a bending force perpendicular to its longitudinal direction having a value of 60 N or less, preferably 45 N or less, particularly preferred 39 N or less and/or 15 N or more, preferably 21 N or more, particularly preferred 27 N or more. In a particularly preferred embodiment of the invention, the action of a bending force of 33 N (±6 N) on the application wand leads to a flexural elongation of 5% (at a temperature of 20±2° C.).

In this embodiment, the flexural elongation is measured with a 3 point bending device, where the bending force acts on the bending section of the application wand while the front and the rear sections of the application wand are each supported by a contact surface 311 and 312, the 3 point bending device having an effective span 340 between supports 309 and 310 of between approximately 40 mm and 60 mm.

With regard to the definition of "flexural elongation", flexural elongation is measured according to ISO Standard EN 178 (June 2003) (see Exhibit A), the content of which is incorporated in its entirety into the disclosure herein by reference.

Alternatively or additionally, the application wand may be designed in such a way that the bending section of the wand will flex approximately s=5 mm to 8 mm (in particular s=about 6.4 mm) when placed in a 3 point bending device having an effective span (St) 340 between approximately 40 mm and 60 mm (in particular 48 mm) and subjected to an applied force between 21 N and 45 N, in particular approximately 33 N, on the bending section, perpendicular to the longitudinal direction of the application wand, the wand (at a temperature of 20±2° C.). For a wand thickness (thickness of the wand in the direction of the bending force (h)) of 3 mm in the area of the bending section and a deflection of 6.4 mm, applying the formula below of ISO Standard EN 178, a flexural elongation of 5% results, as follows: $\varepsilon_f$=600*s*h/St$^2$%

In order to increase the safety during use of the application aid, it has proven to be expedient to design the application wand such that at a conventional deflection it is resistant to break. In other words, the application wand is particularly elastically deflectable in a direction transverse to its longitudinal direction, before it breaks or snaps. It has been found that an application wand presenting an elongation at break ($\varepsilon_{f\,B}$) of 6% or more, preferably 8% or more, in particular approximately 16% and/or 50% or less, is sufficiently resistant to break (break-proof).

Within the framework of the specification and the claims herein, the term "elongation at break" ($\varepsilon_{f\,B}$) denotes the flexural elongation, defined according to ISO Standard EN 178 (Exhibit A), at which the application wand breaks for the first time. Maintaining an upper elongation at a break limit of 50% may be helpful to prevent the exertion of excessive force on the wound.

Preferably, in this arrangement, the bending force acts on the bending section of the application wand, while the front and rear wand sections are each supported by a contact surface of a 3 point bending device having an effective span between approximately 40 mm and approximately 60 mm.

Alternatively or additionally, the application wand will be equipped in such a way that, in a 3-point bending device having an effective span (St) between approximately 40 mm and 60 mm (in particular St=48 mm), when subject to a bending force on the bending section perpendicular to the longitudinal direction of the application wand, it does not break or snap, even when there is a deflection of the application wand perpendicular to its longitudinal direction of s=20 mm (at a temperature of 20±2° C.).

According to an additional aspect, the invention herein relates to an application aid having a bendable application wand and wound cleansing head fastened to a front section of the application wand, in particular in the form of a wound cleansing pad or a wound cleansing wipe. A wound cleansing wipe shall be understood to be a natural and/or synthetic textile suitable for cleansing a wound.

Good cleansing action results from the fact that the wound cleansing head has a fiber pad, in particular a fiber pad having synthetic fibers, which preferably have a fiber strength between 0.5 dtex and 20 dtex. In preferred embodiments of the invention, the fiber strength will be between 3 dtex and 12 dtex, particularly between 5 dtex and 8 dtex. A particularly preferred embodiment of the invention includes a mixture of fibers having a strength of approximately 3.3 dtex and approximately 6.7 dtex at a mixing ratio of approximately 50:50. (1 dtex=g/10,000 m).

In this arrangement, the fiber pad can have at least one support layer and threads of synthetic fibers, in particular plastic fibers, arranged on the support layer and projecting from the support layer, preferably forming a pile having a pile height between 3 mm and 30 mm. In other embodiments of the invention, the pile height will be between 3 mm and 13 mm; particularly preferred pile height will be 8 mm to 12 mm. The pile may be formed of fibers of different fiber strengths. Fibers of different materials may also be used to form the pile. In all cases, a fiber strength of all the fibers between 0.5 dtex and 20 dtex is preferred. The cleansing effect can be further improved by the threads having ends or end faces running at an angle to their longitudinal extension and preferably cut off.

With regard to the structure and characteristics of the wound cleansing head, usable according to the invention, reference is made to Publications WO 2010/085831 A1 and US 2015/030,5945 A1, the contents of which are fully incorporated in their entireties into the disclosure herein by reference. The wound cleansing head, which is fastenable or fastened to the front end of the application wand of the application aid according to the invention may have some or all the features of the wound cleansing assembly described in these publications, individually or in any combination.

In embodiments of the invention, the wound cleansing head comprises absorption means capable of absorbing fluids emerging from the wound, like wound exudates. Said absorption means may comprise gel-forming fibers capable of absorbing considerable amounts of fluids. A diagnostic unit capable of analyzing fluids absorbed by the absorption means may be associated with the absorption means.

Wound cleansing devices comprising gel-forming fibers and/or diagnostic units capable of analyzing fluids emerging from the wound are disclosed in Int'l (PCT) Pub. No. WO2020/245656 A1, incorporated herein by reference to the same extend as if this publication was added to the current application.

Any injury of the wound by the application wand can be reliably prevented by having the wound cleansing head completely encircling or enveloping the front section of the application wand. In particular, the wound cleansing head partially or completely encircles the fastening section of the application wand designed for fastening the wound cleansing head.

In some embodiments, the wound cleansing head may be arranged on the fastening section 24 of the application wand in such a way that it completely envelopes the fastening section, in the direction toward the rear section, to allow the application wand to exit via a reach through opening 51 formed in the wound cleansing head at its rear end.

Alternatively or additionally, the wound cleansing head completely encircles the front section of the application wand, a first layer of the wound cleansing head, designed as a wound cleansing wipe, being arranged on a first side of the application wand (e.g. upper) and a second layer of the wound cleansing head arranged on the opposite side of the application wand (e.g. lower), so that the front section 72 of the application wand is arranged between the two layers. The wound cleansing head may, for instance, have a pad or wipe wound once or more times around the front section 72 of the application wand.

Detachment of the wound cleansing head from the application wand during wound treatment can be prevented by a high bond strength (force required to pull the wound cleansing head from the application wand) between the application wand and the wound treatment head. Preferably, in the longitudinal direction of the application wand, the bond strength between the wound treatment head and the application wand during extraction of the wound cleansing head from the application wand will be greater than 25 N, particularly preferred greater than 50 N. In particular, the bond strength will be 70 N or greater. A bond strength of 70 N or more shall, according to the invention, be understood to mean that the wound cleansing head does not become detached from the application wand when an extraction force of 70 N or more is applied to pull it in the longitudinal direction of the application wand.

In a particularly preferred embodiment of the invention, the wound cleansing head has a reach-through opening 51 through which the application wand moves and through which the application wand can exit the wound cleansing head in the direction of the rear section. The fastening section of the application wand, around which the wound cleansing head circles, may have projections 27, such as barbs, that project from the application wand and prevent the application wand from sliding out through the reach-through opening, thereby helping to retain the wound cleansing head. In this way, the bond strength between the application wand and the wound cleansing head can be further enhanced.

Alternatively or additionally, the wound cleansing head may be fastened to the application wand by one or a plurality of fastening seams. For instance, the front edge 54 of the wound cleansing head and/or the opposing rear edge 52 of the wound cleansing head, which faces the grasping handle section of the application wand, has at least one fastening seam.

The bond strength can be further enhanced by the rear edge of the wound cleansing head facing the grasping handle section, which has a fastening seam on both sides of the application wand. For instance, the rear edge of the wound cleansing head facing the grasping handle section can be cross-joined by sewing to a step or a projection of the application wand. In this way, extraction of the wound cleansing head from the application wand can be reliably prevented. In particular, the application wand can be prevented from accidentally sliding through a reach-through opening of the wound cleansing head during in wound treatment.

Safety of the invention when used in the area of invasive surgery can be improved by providing for at least one of the fastening seams with an X ray contrast thread (RC thread), especially a barium sulfate-laden plastic thread. An RC thread can, for instance, be provided with a barium sulfate-laden polypropylene.

Alternatively or additionally, the application aid according to the invention may have RC chips, RC platelets and/or other X-ray contrast agents incorporated therein or disposed thereon.

In order to further increase the bond strength between the application wand and the wound treatment head, it has proven to be expedient for the application wand to have an opening or a recess, through which the wound treatment head can be additionally secured to the application wand. For instance, a layer of the wound cleansing head arranged on an upper side of the application wand is connected and/or joined by sewing, through the opening 29, to a layer of the wound cleansing head arranged on a lower side of the application wand.

The application wand may have this opening in its front section, the opening being, for instance, designed as a slot extending in the longitudinal direction of the application wand. A slot opening is particularly suitable for stitching a secure seam through the application wand. The slot opening may have a length of 1 cm or more, or 2 cm or more and/or 5 cm or less.

Alternatively or additionally, the wound cleansing head may be fastened to the application wand by ultrasonic welding.

Further, alternatively or additionally, the wound cleansing head may be fastened to the application wand by one or a plurality of barbs. The application wand may, for instance, have one or a plurality of barbs in its fastening section, that project from the application wand and secure the wound cleansing head to the application wand.

Alternatively or additionally, the wound cleansing head will be fastened to the application wand using an adhesive agent. The wound cleansing head may, for instance, be glued to the application wand. Using an adhesive, a particularly high bond strength can be provided.

Alternatively or additionally, the wound cleansing head may be fastened to the application wand using a preferably releasable click system. In this way, reuse of the wand and/or the pads can be made possible.

Alternatively or additionally, the wound cleansing head may be fastened to the application wand using a hook and loop fastener. In this way, reuse of the wand and/or pads can be made possible.

Alternatively or additionally, the wound cleansing head may be fastened to the application wand using a molded closure.

The wound cleansing head may have dimensions adapted to the intended application. A small wound cleansing head can, for instance, can be more conveniently used for wound pockets.

In a preferred embodiment of the invention, the length of the wound cleansing head in the longitudinal direction of the application wand will be 3 cm or more and 10 cm or less, particularly approximately 5 cm.

In this arrangement, the width of the wound cleansing head in a width direction perpendicular to the longitudinal direction of the application wand can be 1 cm or more and 5 cm or less, in particular approximately 2 cm.

Recognition of the wound depth by the user can be made possible by the application wand being provided with a length scale 31. The length scale can indicate the distance of one or a plurality of positions on the application wand from the front end of the application wand.

Alternatively or additionally, other labels, logos, bar codes, QR codes, RFID chips or similar may be arranged on the application wand, in order to provide the user with additional information.

In a particularly preferred embodiment of the invention, a grasping handle section of the application wand is designed slip-proof so that it can even be grasped wearing gloves, without the risk of slipping off.

For the purpose of improving the grip of the grasping handle section, it has proven to be expedient to provide the grasping handle section with a profile, in particular a corrugation, a cross sectional profile expanding at least sectionally in the longitudinal direction of the application wand toward its rear end and/or an ergonomic shape to increase skid resistance.

Figure 5A:
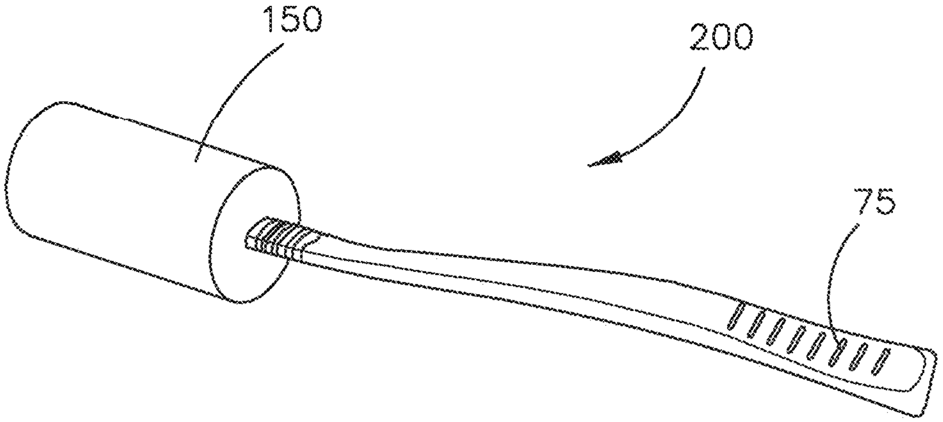
FIG. 5*a* An elevation view of an application aid and wound cleansing head according to another embodiment of the invention herein.
Figure 5B:
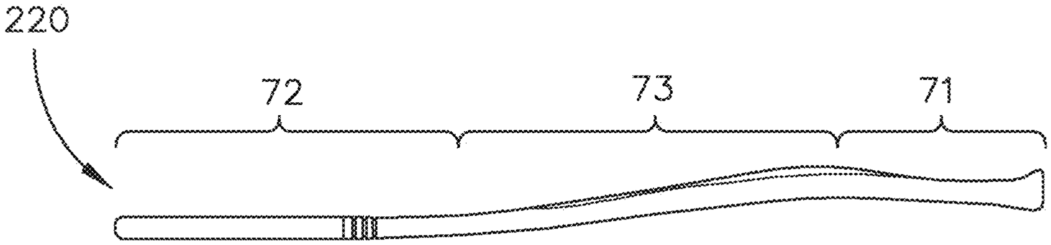
FIG. 5*b* A schematic side profile view of another embodiment of an application aid according to the invention.

The handling of the application aid according to the invention can be further improved by the application wand being at least sectionally bent or curved, as exemplified in FIG. 5*b*. A rear section of the application wand, for instance, extends substantially in a first plane and a front section of the application wand extends substantially in a second plane that is offset with respect to the first plane, the middle section of the application wand running curved from the first plane into the second plane. This can provide for a trowel-shaped application wand course, which may, for instance, be preferred for use with deep wounds.

The manufacture of the application wand can be simplified by having it, at least partially and preferably entirely, molded of materials such as plastic, polypropylene. The application wand may, for instance, be molded in one piece from plastic.

For the treatment of deep wounds a suitable overall application wand length L is at or between approximately 10 cm and approximately 20 cm, particularly approximately 15 to 16, cm.

In embodiments of the invention the cross-sectional area of the flexible bending section and/or the wound cleansing head in a plane extending perpendicular to the longitudinal direction is less than 100 $mm^2$, preferably 25 $mm^2$ or less, more preferably 10 $mm^2$ or less.

The aspect ratio of the flexible bending section and/or the wound cleansing head may be 2 or less, preferably 1.5 or less. The aspect ratio within the meaning of this description and the claim specifies the ratio between the largest dimension in a plane extending perpendicular to the longitudinal direction and the smallest dimension in a plane extending perpendicular to the longitudinal direction. In embodiments of the invention, the application aid has an essentially circular cross-sectional area in a plane extending perpendicular to the longitudinal direction. In this case, the aspect ratio is about 1.

In an application aid according to the invention, a portion of the bending section may be made of a material of lower flexural strength than the sections adjacent to the bending section.

The application aid may be sterile or sterilized for application in wounds.

In the following description the embodiments of the invention are provided with reference to the accompanying drawings and those of US 2015/0305945 A1, which are incorporated herein by reference in their entireties.

FIG. 1 shows an embodiment of the application aid 10 according to the invention in a schematic upper side view. Application aid 10 consists of a bendable application wand 20 and a wound cleansing head 50 which in this embodiment is provided as a wound cleansing pad, which is fastened to a front section of application wand 20.

Figure 2:
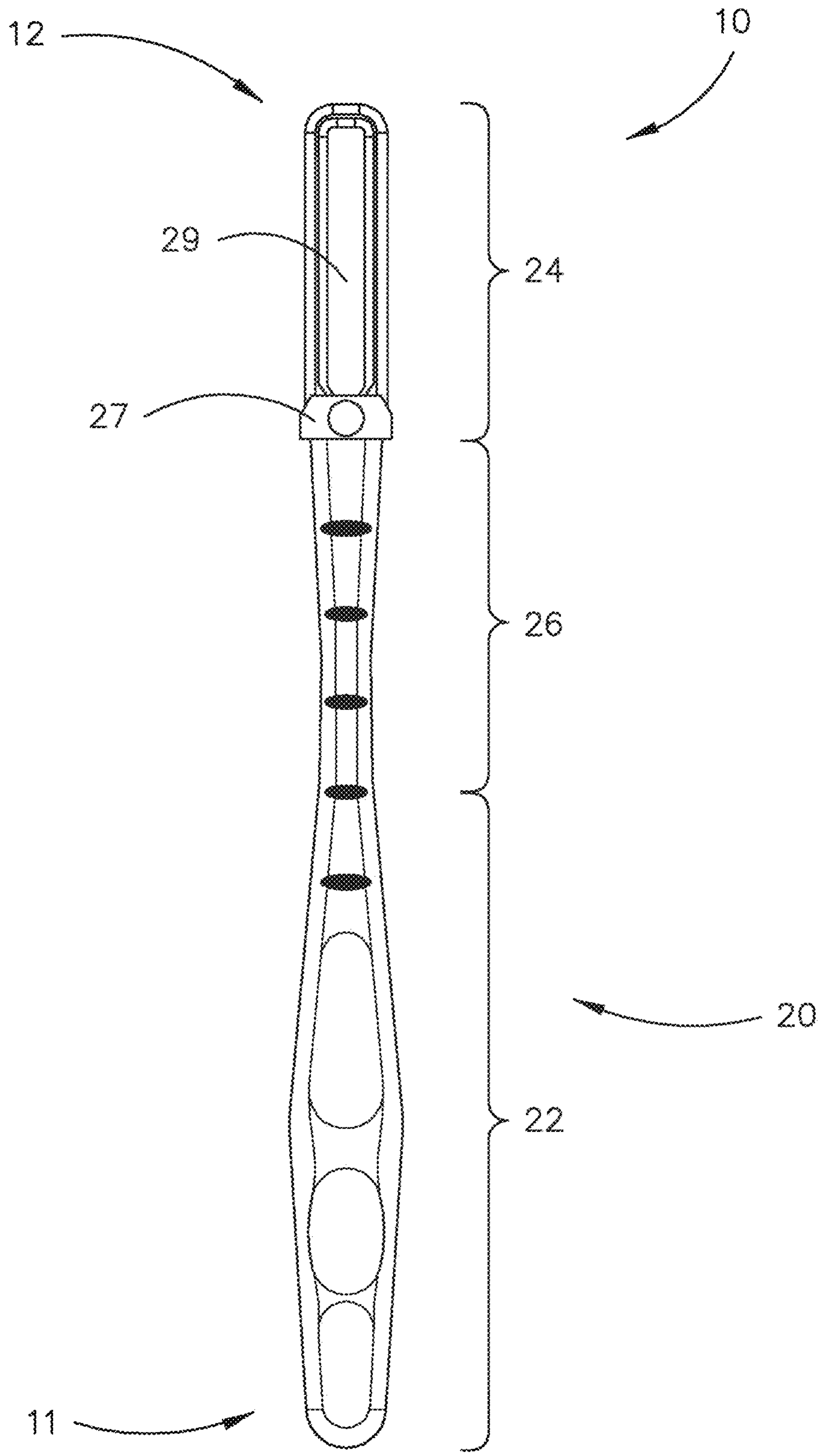
FIG. 2 A schematic upper side view of an one embodiment of the application aid according to the invention.

FIG. 2 shows application wand 20 of FIG. 1, without wound cleansing head 50 fastened thereto. A rear section of application wand 20 is designed as grasping handle section 22, a middle section of application wand 20 is designed as bending section 26 having increased flexibility, and the front end of the application wand is designed as fastening section 24 for fastening a wound cleansing head 50.

In the embodiment illustrated in FIG. 1, wound cleansing head 50, only schematically indicated, encircles fastening section 24 completely, so that, when treating wounds using application aid 10, any direct contact between the wound and the front section of the application wand 20 is avoided.

Application wand 20 extends in a longitudinal direction and preferably has an overall length L between approximately 10 cm and approximately 20 cm, in particular approximately 15 to 16 cm. Grasping handle section 22 may extend over approximately half of the total length of the application wand, while the fastening section may be adjusted to the length of the wound cleansing head (X, exemplified in FIG. 1) and may, for example, have a length of approximately 5 cm. In a preferred embodiment, the wound cleansing head has a length of approximately 5 cm and a width B of approximately 2 cm to 3 cm.

Figure 3:
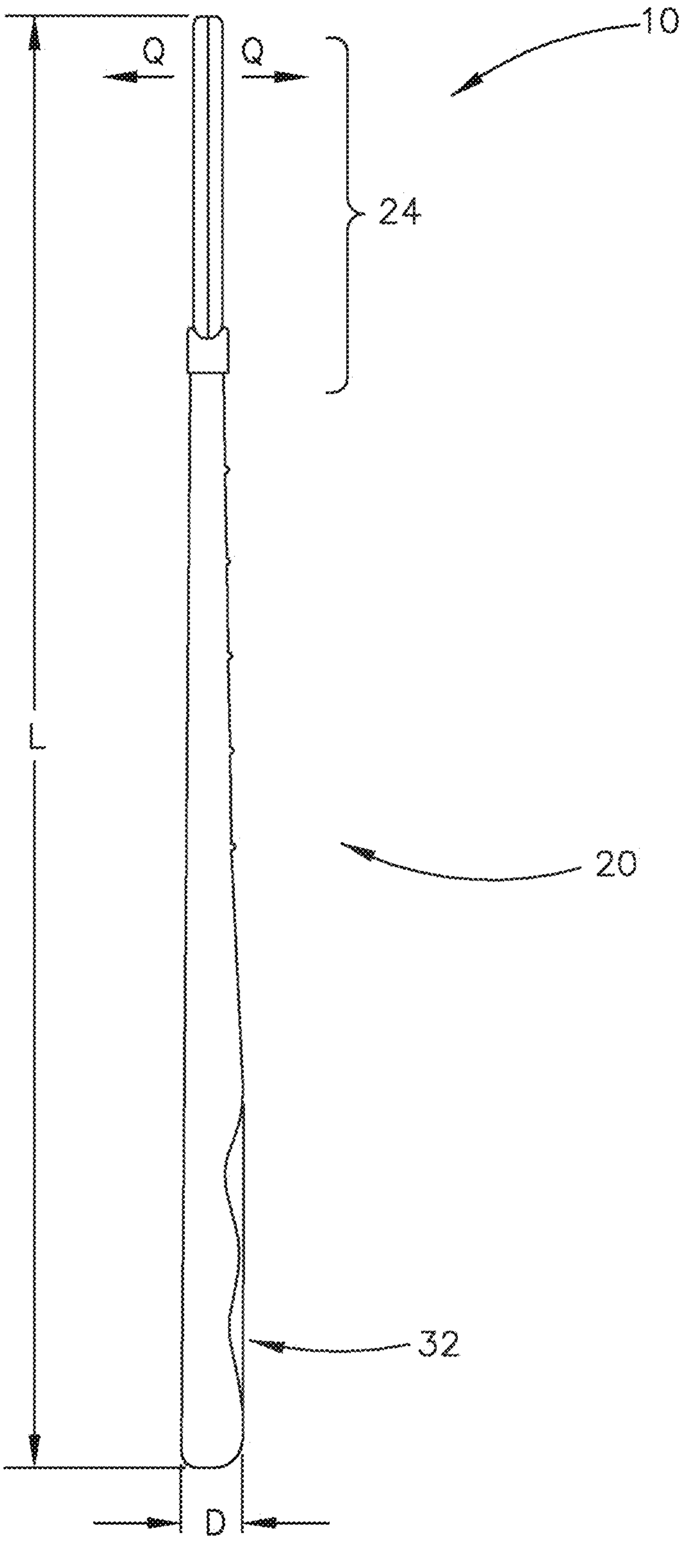
FIG. 3 A schematic side profile view illustrating a profile of the application wand shown in FIG. 2, rotated 90° and showing an upper side and lower side of the wand.

In grasping handle section 22, application wand 20 may have profile 32, such as a corrugation for improving its grip, and furthermore, it may have a thickness which decreases toward the wound cleansing head 50, as exemplified in FIG. 3.

FIG. 3 shows another embodiment of an application wand 20 of an application aid 10 according to the invention in side profile view (rotated 90° compared to upper side view of FIG. 2). The maximum thickness D of the application wand in grasping handle section 22 may be approximately 5 to 7 mm, while bending section 26 may have a thickness of only approximately 2 to 4 mm, in particular approximately 3 mm.

FIGS. 1 and 2 additionally show, arranged in bending section 26 and in a forward portion of grasping handle section 22, a scale 31 for reading depth of a wound.

Application wand 20 is elastically deformable and returns to its unstressed state when deflected in a transverse direction Q (shown by arrows in FIG. 3). In this arrangement, the flexural rigidity of application wand 20 is established in such a way that, upon an excessive exertion of pressure by the user, the application wand is deflected, thereby allowing injuries of the target wound to be prevented. Simultaneously, the bending stiffness is sufficiently high so that the user does not lose the feeling for the force being applied.

The flexibility of the application wand is in particular arranged in such a way that, upon applying a bending force to the application wand perpendicular to its longitudinal direction at a value between 21 N and 45 N, in particular approximately 33 N, a flexural elongation of the application wand of approximately 5% results.

With reference to FIG. 7, hereinafter, a method for determining the flexural elongation of an application wand using a 3 point bending device is exemplified, measurement performed in accordance with the method described in DIN Standard EN ISO 178.

Figure 7A:
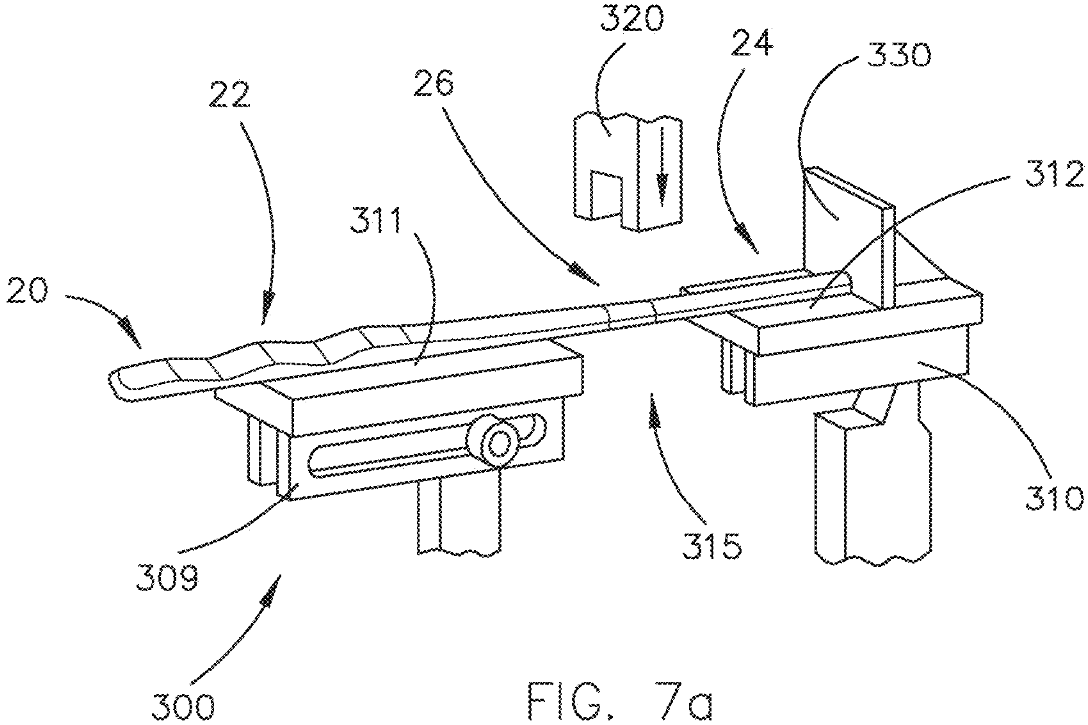
FIG. 7*b* A side view of a 3 point bending device showing direction of exertion of force (arrow) by pressure pane on application aid according to the invention.

FIG. 7*a* shows of a 3 point testing instrument 300 having supports 309 and 310 and a pressure pane 320 arranged above it. Support 309 has a first contact surface 311 for supporting grasping handle section 22 of an application wand and support 310 has a second contact surface 312 for supporting fastening section 24 of application wand 20 at a predetermined distance from the grasping handle section 22. Bending section 26 of the application wand is arranged above the interstice 315 between the two supports 309, 310, the interstice has an effective span (St) of between approximately 40 mm or more, and approximately 60 mm or less, in particular approximately 48 mm. A vertical impact surface 330 facilitates the correct positioning of the application wand on support 310.

Figure 7B:
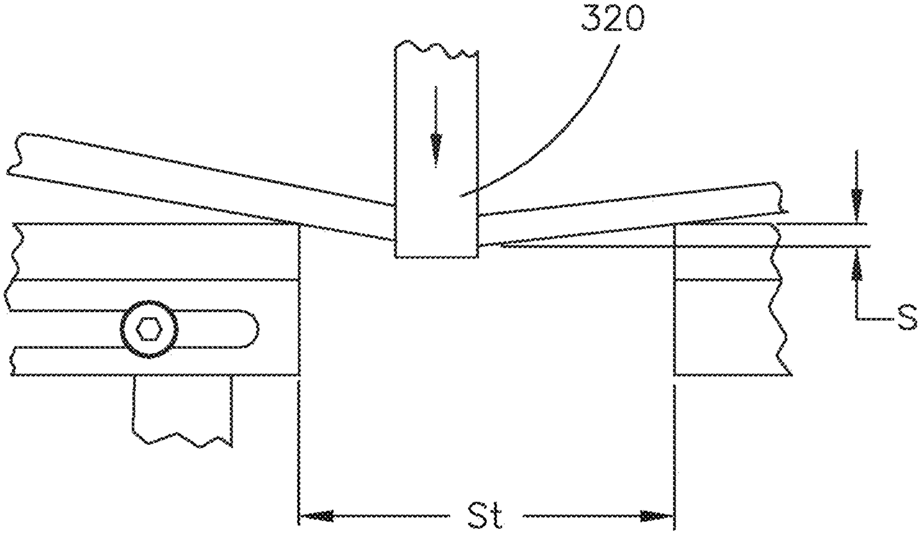

Pressure pane 320 has, at its lower end, a pressure surface and is equipped to be movable perpendicular to the longitudinal direction of the application wand. As shown in FIG. 7*b*, pressure pane 320 exerts a bending force on application wand 20 from above (in direction of arrow), and is moved into the interstice 315 between the two contact surfaces all the way to a predetermined end position as exemplified in FIG. 7*b*. This results in specified deflection (indicated by distance "s") of the application wand perpendicular to its longitudinal direction. The bending force exerted on the application wand by pressure pane 320 in the end position can be measured.

For a wand diameter of 3 mm in the bending section on which the bending force acts, a deflection of approximately 6.4 mm results in a flexural elongation of 5% (derived from the formula $\varepsilon_f$=600*s*h/St$^2$%). For such a flexural elongation, preferably a bending force between approximately 21 N and 45 N should be required, in particular a bending force of approximately 33 N. As such, an application wand satisfies the preferred bending properties in particular when a pressure force of approximately 33 N exerted by the pressure pane results in a deflection of between approximately 5 mm and approximately 8 mm, in particular approximately 6.4 mm.

Furthermore, the application wand according to the invention is preferably equipped to be break-proof at a bending load. The application wand should, in particular, not break or snap at a flexural elongation of 8%, in particular not even at a flexural elongation of 16%. Using the measuring device shown in FIGS. 7*a* and 7*b*, it is possible to measure whether an application wand has the desired breaking resistance. The breaking resistance can be measured on an application wand having a wound cleansing head fastened to it.

Measurement of Elongation at Break

As exemplified in FIGS. 7*a* and 7*b*, application wand 20 is placed on supports 309 and 310 of the testing instrument 300, as described above, and for exerting a bending force on bending section 26 of the application wand, pressure pane 320 is moved into the interstice between the two contact surfaces 311, 312 having an effective span (St) between 40 mm and 60 mm, in particular approximately 48 mm.

If, at a deflection (s) of s=20 mm, application wand 20 does not yet break or snap, and withstands a flexural elongation of 16% or more, it satisfies the preferred characteristics according to the invention in terms of its resistance to break.

Securing of Wound Cleansing Head to Application Wand

In application aid 10 according to the invention, wound cleansing head 50 is fastened to application wand 20 with a high bond strength of 70 N or more. In other words, the wound cleansing head does not release from application wand 20 when wound cleansing head 50 is moved upward (see FIG. 1) using a tensile force of 70 N, 75 N or more in the longitudinal direction of application wand 20. In a practical application of application aid 10 for cleansing a wound, this prevents the wound cleansing head 50 from being released from the application wand when it is pulled from the wound. For securely connecting wound cleansing head 50 to application wand 20, a bond strength of 70 N has proven to be particularly helpful. In practice, however, even a bond strength in a range of 50 N or more may also be sufficient.

The bond strength between application wand 20 and wound cleansing head 50 can be measured using an art recognized tension testing instrument having a fastener for fastening the application wand and a retraction device for pulling the wound cleansing head, the fastener and the retraction device being capable of being pulled apart at a specified tensile force. The tensile force required for releasing the wound cleansing head from the application wand can be determined in this way.

A wound cleansing head 50 may be fastened to application wand 20 using one or a plurality of fastening seams. A wound cleansing head, for example, may be sewn on both sides of its rear edge 52 and at its front edge 54.

Alternatively, a wound cleansing head 50 may be sewn through an opening 29 of application wand 20. For example, layer of wound cleansing head 50 arranged toward front edge 54 of opening 29 is, for instance, sewn to a layer of wound cleansing head 50 arranged at rear edge 52 of wound cleansing head, in order to secure the connection between application wand 20 and the wound cleansing head.

In this arrangement, at least one sewing thread may have X-ray contrast capacity and may, for instance, be designed as a barium sulfate-laden plastic thread. This RC thread (not shown), for example can encircle the application wand 20 at the rear edge 52 of the wound cleansing head (FIG. 1).

Furthermore, wound cleansing head 50 may include a reach-through opening 51 traversed by application wand 20 at its lower end in FIG. 1, thereby causing the prevention of extraction of application wand 20 through opening 51 by projections 27 or barbs, which project from application wand 20 outward in a width direction.

Figure 4A:
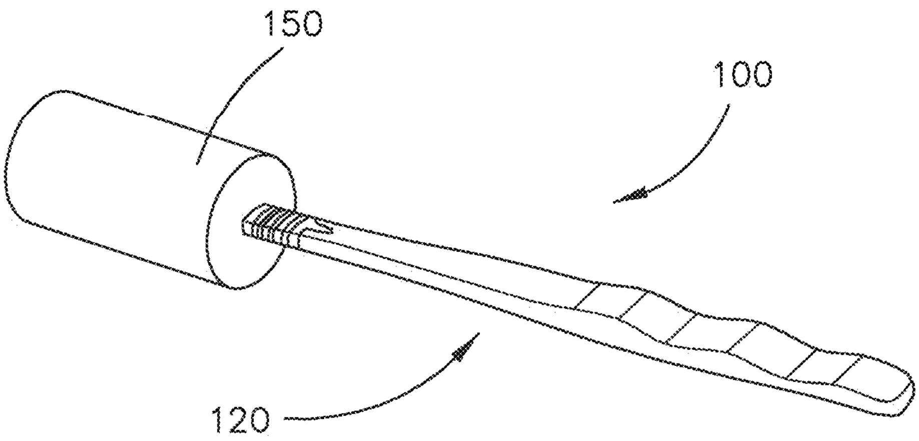
FIG. 4*a* An elevation view an application aid and wound cleansing head according to one embodiment of the invention herein.

FIG. 4*a* shows an additional embodiment of an application aid 100 according to the invention, having an application wand 120 and a wound cleansing head 150, arranged on the fastening section of the application wand.

Figure 4B:
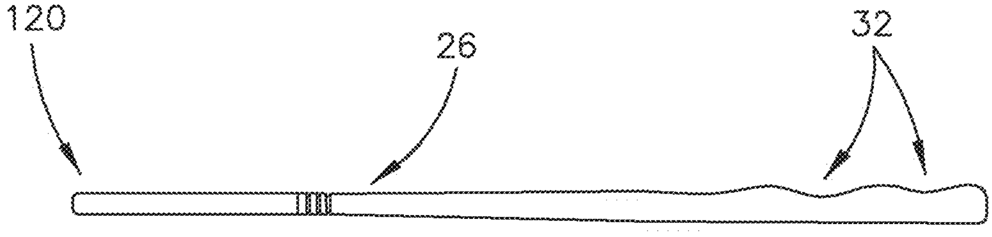
FIG. 4*b* A schematic side profile view of another embodiment of an application aid according to the invention.
Figure 4C:
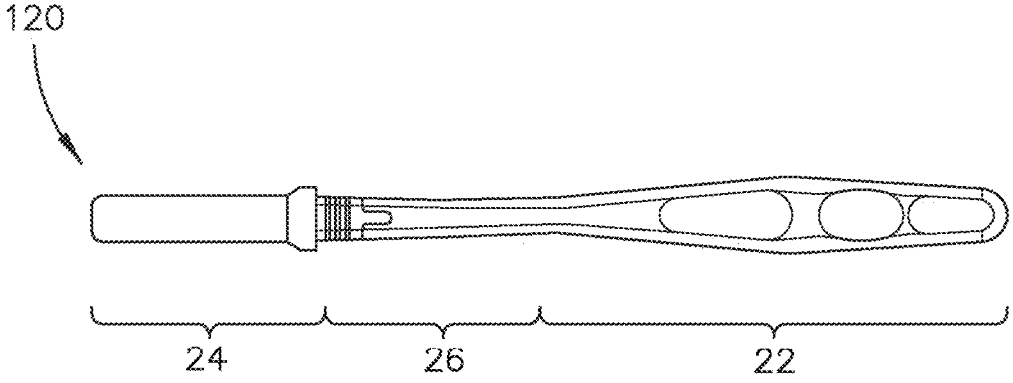
FIG. 4*c* A schematic side view rotated 90° of another embodiment of the application aid according to the invention.

FIG. 4*b* shows application wand 120 in a first side view, and FIG. 4*c* shows application wand 120 in a side view rotated 90°.

FIGS. 4*b* and 4*c* clearly show that the near the rear end in another embodiment of the application wand 120 may be designed as a grasping handle section having profile 32 in the form of corrugations. For achieving a particularly ergonomic shape with good slip resistance, the cross section of the grasping handle section 22 is tapered towards bending section 26.

For increased the flexibility, the application wand 120 may include notches or depressions in bending section 26. These notches are arranged in an area of bending section 26, which comprises a material different from that of the areas adjacent to bending section 26. This material is selected in such a way that it provides bending section 26 increased flexibility. This material may, for instance, comprise an elastomer.

In the embodiment of FIGS. 4*a* and 4*b*, application wand 120 extends substantially linearly and does not have any bends.

FIG. 5*a* shows an additional embodiment of an application aid 200 according to the invention, which has an application wand 220 and, arranged on the fastening section of the latter, a wound cleansing head 150.

Figure 5C:
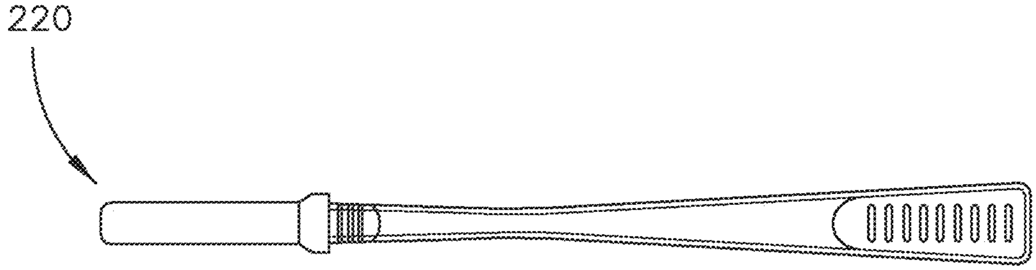
FIG. 5*c* A schematic side view rotated 90° of another embodiment of the application aid according to the invention.

FIG. 5*b* shows application wand 220 in a first side view, and FIG. 5*c* shows application wand 220 in a side view rotated 90°. Application wand 220 corresponds substantially in other respects to the above described application wands 20, 120, so that reference can be made to the above explanations.

In the embodiment of the invention exemplified in FIG. 5*b*, in contrast to application wand 120 of FIG. 4*b*, sections of application wand 220 are curved to improve handling. The side profile view presented in FIG. 5*b* shows that the longitudinal course of the application wand approaches a trowel shape, in which a section 71 near the rear end of the application wand runs substantially in a first plane and a section 72 nearer the front end of the application wand runs substantially in a second plane that is offset with respect to the first plane, and an intermediate section 73 of the application wand curves from the first plane into the second plane.

Alternatively, instead of a profile 32 designed as corrugation, application wand 220 may include rifling or ribs 75, to increase slip resistance (FIG. 5*a*).

Figure 6A:
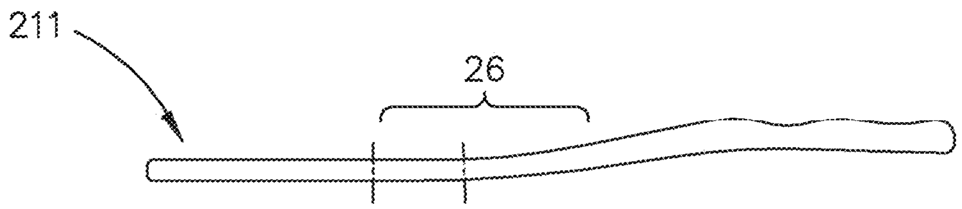
FIG. 6*a* A schematic side profile view of a further embodiment of the application aid according to the invention.
Figure 6B:
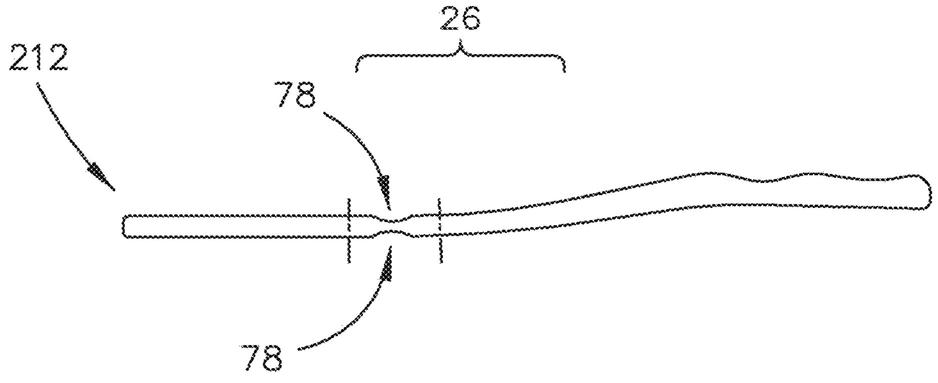
FIG. 6*b* A schematic side profile view of a yet further embodiment of the application aid according to the invention.
Figure 6C:
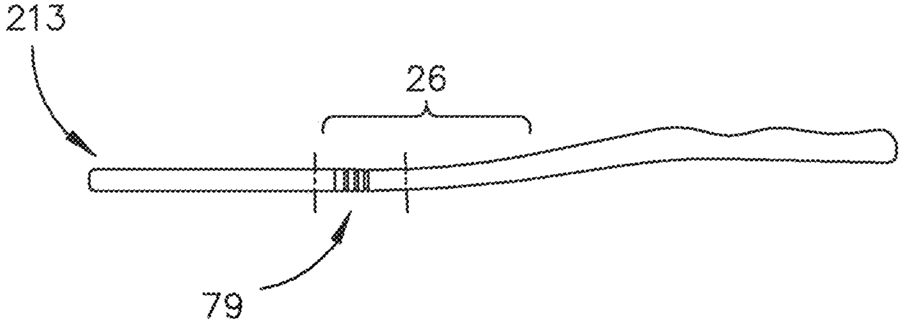
FIG. 6*c* A schematic side profile view of a yet another embodiment of the application aid according to the invention, and FIG. 7*a* A schematic elevation view of a 3 point bending device showing placement of an application aid according to the invention for measuring the flexibility of the application wand.

FIGS. 6*a* to 6*c* show various other embodiments of embodiments of the application wands 211, 212, 213 of application aids according to the invention, each presented in a side profile view.

Application wand 211 shown in FIG. 6*a*, in its bending section 26, has a substantially constant cross section. The application wand 212 shown in FIG. 6*b* has a taper in the form of two notches 78 introduced into bending section 26 from opposite sides of the application wand, the orientation of the notches running perpendicular to a main longitudinal direction of the application wand. The embodiment of the application wand 213 shown in FIG. 6*c* has a plurality of circumferential notches 79 running perpendicular to the longitudinal direction of the application wand, which increase the flexibility of the application wand in both transverse directions. In this embodiment the notches 79 are located in the bending section 26, which comprises a material that is different from that of the areas adjacent to bending section 26. This material is designed in such a way that it provides bending section 26 with increased flexibility. This material may, for instance, comprise an elastomer.

Structure and Characteristics of Wound Cleansing Head

With regard to the structure and the characteristics of various embodiments of a wound cleansing head 50, reference is made to the disclosures and drawings of Publications A 145/2009 (AT), WO 2010/085831 A1, US 2012/0046670 A1 and US2015/0305945 A1, which are incorporated herein by reference in their entireties. Preferably, the wound cleansing head comprises polyester fibers, preferably polyester fibers of polypropylene, for the effective removal of debris and exudate from the wound and scales and keratoses from the skin surrounding the wound. A soft fiber bundle can conveniently reduce potential pain from use of the application wand.

The break-proof grasping handle, preferably of polypropylene, provides easy access to deep wounds and hard to reach wound locations.

Highest application safety can be assured by precise fastening seams, an ergonomic handle and traceable x-ray contrast threads.

Before cleansing a wound, the wound cleansing head can be wetted using a wound irrigation solution.

Since many possible embodiments may be made of the invention without departing from the scope thereof, it is to be understood that all matters herein set forth or shown in the accompanying drawings are to be interpreted as illustrative, and not in a limiting sense. While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations, all of which are contemplated by and are within the scope of the claims.

What is claimed and desired to be secured by Letters Patent is as follows:

1. An application aid for debriding or cleansing of wounds comprising a bendable application wand having a rear end and a front end, a longitudinal direction, a front section adjacent the front end, a rear section adjacent the rear end, two opposite sides, and a cross section, said application wand further comprising a flexible bending section between the front section and the rear section, said bending section having greater flexibility than the front section and the rear section, wherein at least a portion of the bending section comprises a material of lower flexural rigidity than the rigidity of a material of the front section and of the rear section, wherein the front section holds a wound cleansing head, the wound cleansing head comprising a fiber wound cleansing pad or fiber wound cleansing wipe comprising synthetic fibers, wherein the front section of the application wand comprises a fastening section for holding the wound cleansing head and the rear section comprises a grasping handle section, and wherein the wound cleansing head is fastened to the application wand by one or more fastening seams.

2. The application aid according to claim 1, characterized in that the bending section of the application wand comprises a reduced cross section compared to grasping handle section, and/or a notch or depression that extends in a direction transverse to the longitudinal direction of the application wand, said reduced cross section and/or notch provide increased flexibility to the bending section.

3. The application aid according to claim 1, where the grasping handle section extends over more than ⅓ and less than ⅔ of the longitudinal direction of application wand and the fastening section extends over more than ⅕ and less than ⅓ of the longitudinal direction of the application wand.

4. The application aid according to claim 1, characterized in that a bending force of between approximately 60 Newton (N) and approximately 15 N acting on the application wand perpendicular to its longitudinal direction results in a flexural elongation of approximately 5%.

5. The application aid according to claim 4, where the flexural elongation of approximately 5% results from a bending force of between 21 N and approximately 33 N.

6. The application aid according to claim 1, characterized in that the application wand is deflected by 5 mm to 8 mm when a bending force of between 21 N and 45 N is applied to the bending section perpendicular to the longitudinal direction of the application wand, the bending force applied using a 3 point bending device having two supports and a span between the supports, where the length of span between supports is between 40 mm and 60 mm.

7. The application aid according to claim 1, characterized in that the application wand has an elongation at break of between 6% and 50%.

8. The application aid according to claim 7, where the application wand has an elongation at break of 16%.

9. The application aid according to claim 1, characterized in that the application wand resists breaking when a bending force is applied to the bending section perpendicular to the longitudinal direction of the application wand causing a deflection of the application wand of up to 20 mm, the bending force applied using a 3 point bending device having two supports and a span between the supports, where the length of span between supports is between 40 mm and 60 mm.

10. The application aid according to claim 1, wherein said synthetic fibers have a fiber strength of between 0.5 dtex and 20 dtex.

11. The application aid according to claim 1, characterized in that the fiber wound cleansing pad or wipe comprises at least one support layer and threads arranged on the support layer, the threads projecting longitudinally from the support layer to form a pile with a pile height of between 3 mm and 30 mm, at least some of the threads comprising ends or end faces extending away from the support layer at an angle to their longitudinal projection.

12. The application aid according to claim 11, where the ends or end faces of the threads are cut off.

13. The application aid according to claim 1, characterized in that the wound cleansing head completely encircles or envelopes the fastening section of the application wand.

14. The application aid according to claim 1, where the force required to remove the wound cleansing head from the fastening section in the direction of the longitudinal direction of the application wand is more than 25 N.

15. The application aid according to claim 14, where the force required to remove the wound cleansing head from the fastening section in the direction of the longitudinal direction of the application wand is 70 N or more.

16. The application aid according to claim 1, characterized in that the wound cleansing head comprises a lower edge facing the grasping handle section and a front edge opposite the lower edge of the wound cleansing head, the lower edge comprising a reach-through opening to facilitate insertion of the application wand into the wound cleansing head, and the fastening section of the application wand comprises projections that help keep the inserted application wand from sliding back through the reach-through opening.

17. The application aid according to claim 1, where a lower edge of the wound cleansing head is fastened to the fastening section with the one or more fastening seams, wherein the one or more fastening seams are located on one or both sides of the application wand, and/or with at least one seam on a front edge of the wound cleansing head.

18. The application aid according to claim 1, characterized in that at least one or more of the fastening seams comprises an X-ray contrast thread.

19. The application aid according to claim 1, the fastening section further comprising a first side and opposite second side and an opening extending from first to second side of the fastening section through which a portion of wound cleansing head arranged on one side of the application wand is sewn to another portion of the wound cleansing head arranged on the opposite side of the application wand.

20. The application aid according to claim 1, characterized in that the wound cleansing head is fastened to the application wand with a holding device selected from the group consisting: of a bonding agent, an ultrasonic weld, a releasable click system, a hook and loop fastener, a molded closure, and one or more barbs.

21. The application aid according to claim 16, characterized in that a distance between the front edge and lower edge of the wound cleansing head is between 3 cm and 10 cm.

22. The application aid according to claim 1, characterized in that wound cleansing head further comprises a width perpendicular to the longitudinal direction of application wand and the width of the wound cleansing head is between 1 cm and 5 cm.

23. The application aid according claim 1, characterized in that the application wand comprises a length scale for determining depth of a wound.

24. The application aid according to claim 1, characterized in that the grasping handle section of the application wand comprises a profile to increase skid resistance, the profile selected from the group consisting of a corrugation, a cross section that increases toward the rear end of the application wand and an ergonomic shape.

25. The application aid according to claim 1, characterized in that the grasping handle section of application wand is sectionally bent or curved to improve handling.

26. The application aid according to claim 1, characterized in that a total length of the application wand is 10 cm or more and 20 cm or less.

27. The application aid according to claim 1, wherein a cross-sectional area of at least one of the flexible bending section and the wound cleansing head, in a plane extending perpendicular to the longitudinal direction, is less than 100 $mm^2$.

28. The application aid according to claim 27, wherein an aspect ratio of at least one of the flexible bending section and the wound cleansing head is 2 or less.

29. The application aid according to claim 1, wherein the wound cleansing head comprises an absorption means.

30. The application aid according to claim 29, wherein the absorption means comprises gel-forming fibers.

31. The application aid according to claim 29, wherein the absorption means has associated therewith a diagnostic unit capable of analyzing fluids absorbed by the absorption means.

32. The application aid according to claim 1, wherein the one or more fastening seams comprise a first fastening seam on both sides of the application wand at the rear edge of the wound cleansing head facing the grasping handle section, wherein the rear edge is cross-joined by sewing to a step or a projection of the application wand.

* * * * *